United States Patent
Priszner (10) Patent No.: US 10,188,846 B1
(45) Date of Patent: Jan. 29, 2019

(54) TWO-WAY RETRACTABLE MEDICAL TUBING REEL

(71) Applicant: Roy L. Priszner, Franklin, TN (US)

(72) Inventor: Roy L. Priszner, Franklin, TN (US)

( * ) Notice: Subject to any disclaimer, the term of this patent is extended or adjusted under 35 U.S.C. 154(b) by 388 days.

(21) Appl. No.: 15/173,632

(22) Filed: Jun. 4, 2016

(51) Int. Cl.
*A61M 39/08* (2006.01)
*B65H 75/44* (2006.01)

(52) U.S. Cl.
CPC ......... *A61M 39/08* (2013.01); *B65H 75/4471* (2013.01)

(58) Field of Classification Search
CPC .......................... A61M 39/08; B65H 75/4471
See application file for complete search history.

(56) References Cited

U.S. PATENT DOCUMENTS

| | | | |
|---|---|---|---|
| 3,338,538 A | 8/1967 | Roche | |
| 5,236,143 A * | 8/1993 | Dragon | B65H 75/48 226/187 |
| 5,332,171 A * | 7/1994 | Steff | B65H 75/38 242/378 |
| 6,588,444 B2 * | 7/2003 | Paplow | B65H 75/40 137/15.01 |
| 7,093,783 B2 * | 8/2006 | Warren | B65H 75/48 242/378.1 |
| 7,104,491 B2 * | 9/2006 | Vinding | A61M 39/08 242/378 |
| 7,900,863 B1 * | 3/2011 | Cheng | B65H 75/4431 242/378.1 |
| 7,909,281 B2 * | 3/2011 | Liao | B65H 75/4434 242/378.1 |
| 8,702,025 B2 * | 4/2014 | Kish | B65H 75/4434 242/378.1 |
| 8,707,950 B1 * | 4/2014 | Rubin | A61M 16/06 128/202.27 |
| 2003/0132352 A1 | 7/2003 | Weaver | |
| 2003/0146332 A1 * | 8/2003 | Vinding | A61M 39/08 242/378.4 |
| 2005/0236243 A1 * | 10/2005 | Huang | H02G 11/02 191/12.4 |
| 2006/0261203 A1 * | 11/2006 | Yang | B65H 75/4431 242/378.4 |
| 2007/0181730 A1 * | 8/2007 | Yen | B65H 75/4434 242/378.1 |
| 2009/0090589 A1 * | 4/2009 | Matthew | F21L 14/023 191/12.4 |
| 2009/0277454 A1 * | 11/2009 | Davis | A61M 16/0875 128/207.18 |
| 2010/0307496 A1 * | 12/2010 | Lueckenhoff | A61M 16/0875 128/204.18 |
| 2010/0320304 A1 * | 12/2010 | Iguchi | B65H 75/38 242/388.91 |

(Continued)

*Primary Examiner* — William A. Rivera
*Assistant Examiner* — Mark K Buse
(74) *Attorney, Agent, or Firm* — Shane Cortesi (57) ABSTRACT

A two-way retractable medical tubing system is described. The system includes a housing, a reel located in the housing and a tube wrapped around the reel. The reel is attached to a track that prevents the tube from kinking. The tube has a proximal end and a distal end and exits the housing at a proximal aperture and a distal aperture. Pulling on either the proximal or distal end of the tube causes the tube to partially unwind from the reel so that a longer segment of the tube is located outside the housing as compared when the system is in the retracted position.

17 Claims, 10 Drawing Sheets

(56) References Cited

U.S. PATENT DOCUMENTS

| | | | | |
|---|---|---|---|---|
| 2012/0138724 A1* | 6/2012 | Chen | .................. | B65H 75/4434 |
| | | | | 242/378.1 |
| 2013/0178836 A1* | 7/2013 | Teutsch | ................. | A61M 39/08 |
| | | | | 604/533 |
| 2014/0261766 A1* | 9/2014 | Tracey | ............... | B65H 75/4471 |
| | | | | 137/355.27 |
| 2015/0069164 A1* | 3/2015 | Moore | ............... | B65H 75/4434 |
| | | | | 242/382 |

* cited by examiner

TWO-WAY RETRACTABLE MEDICAL TUBING REEL

BACKGROUND

Technical Field

The present invention relates to reels for use in hospital settings, more particularly, to reels that hold tubing connected to patients, intravenous fluid (IV) bags, and other instruments.

Background of the Invention

In hospital and hospital-type settings (such as nursing homes), there is a need to connect patients to IV fluid bags and other items using medical tubing. Unfortunately, such tubing has a tendency to get tangled, especially since the desired length of the tube can vary from setting to setting.

US Patent Publication No. 2003/0132352 (the '352 publication) teaches an organizer that attaches to a hospital bed in order to secure the various wires and tubes to the hospital bed. The '352 publication does not address the issue of shortening or lengthening the tubes depending on the setting.

U.S. Pat. No. 3,338,538 (the '538 patent) teaches a drainage tube holder for hospital beds. The system of the '538 patent appears overly complex and does not address the issue of shortening or lengthening the tubes depending on the setting.

Thus, there is a need for new systems that manage medical tubes.

BRIEF SUMMARY

The present disclosure provides a two-way retractable medical tubing reel system as described herein.

In some embodiments, the system includes: a housing comprising an interior, an exterior, a top, a bottom, a proximal aperture and a distal aperture; a generally cylindrical reel rotatably mounted in the housing interior and having a reel wall comprising an outer surface having an outer surface circumference, an inner surface having an inner surface circumference, a first wall aperture and a second wall aperture, the reel wall separating a reel exterior from a reel interior; a spindle located in the reel interior; a generally cylindrical spring container located in the reel interior, the spring container comprising a spring attached to the spindle; a track attached to the reel wall and comprising a first end, a U-shaped segment, an internal segment extending from the first wall aperture to the second wall aperture and located between the spring container and the inner wall surface, a second end, and a track length extending from the first end to the second end; a generally hollow tube passing along the track length, wrapped around the outer surface circumference and comprising a proximal end configured to connect to a patient, a distal end configured to connect to an intravenous (IV) fluid bag, and a tube length extending from the proximal end to the distal end, the generally hollow tube passing through the proximal and distal apertures; the generally hollow tube having an extended position wherein a segment of the generally hollow tube is fully enclosed in the housing; the generally hollow tube having a retracted position wherein a longer segment of the tube is fully enclosed in the housing as compared to the extended position and wherein the generally hollow tube wraps around the outer surface circumference a greater number of times as compared to the extended position; wherein the spring is configured to bias the generally hollow tube in the retracted position; and wherein pulling on the proximal end and the distal end of the generally hollow tube in the retracted position is configured to cause the generally cylindrical reel to rotate relative to the housing and move the generally hollow tube to the extended position.

Optionally, at least one of the first and second ends of the track are oriented tangentially relative to the reel wall and the generally hollow tube wraps around the outer surface circumference after exiting the at least one of the first and second ends of the track. Optionally, the track further comprises a floor and at least one curved tab having a first end attached to the floor and a free second end, the at least one curved tab securing the generally hollow tube to the track floor. Optionally, the proximal aperture is located in a proximal face of the housing oriented tangentially relative to the outer surface circumference, wherein the distal aperture is located in a distal face of the housing oriented tangentially relative to the outer surface circumference, the proximal and distal faces located approximately 180 degrees relative to each other and facing opposite directions. Optionally, the first and second wall apertures are located approximately 180 degrees relative to each other. Optionally, the track is located adjacent to the housing bottom. Optionally, the housing interior further comprises a washer located between the housing and the reel outer surface, the washer comprising a washer aperture comprising an indentation located above the track and further wherein two segments of the tube are located between the indentation and the outer surface. Optionally, the proximal end of the tube comprises a proximal end tube fastener configured to removably attach the proximal end to a patient tube connected to the patient, and the distal end of the tube comprises a distal end fastener configured to removably attach the distal end to a IV tube connected to the IV bag. Optionally, the proximal fastener is a luer lock and the distal fastener is a luer lock. Optionally, the proximal fastener is located adjacent to the proximal aperture and the distal fastener is located adjacent to the distal aperture when the generally hollow tube is in the retracted position. Optionally, at least one of the proximal end and the distal end of the generally hollow tube is connected to a sterile spike. Optionally, the housing top is removably attached to the housing bottom. Optionally, the spindle is removably received in a housing aperture located in the housing top. Optionally, the spindle is oriented generally perpendicular to the outer surface circumference and the inner surface circumference.

In still further embodiments, the system includes: a housing comprising an interior, an exterior, a bottom, a top, a proximal side comprising a housing comprising an interior, an exterior, a top, a bottom, a proximal aperture and a distal aperture; a generally cylindrical reel rotatably mounted in the housing interior and having a reel wall comprising an outer surface having an outer surface circumference, an inner surface having an inner surface circumference, the reel wall separating a reel exterior from a reel interior; a generally hollow tube passing along the track length, wrapped around the outer surface circumference and comprising a proximal end configured to connect to a patient, a distal end configured to connect to an intravenous (IV) fluid bag, and a tube length extending from the proximal end to the distal end, the generally hollow tube passing through the proximal and distal apertures; the generally hollow tube system having an extended position wherein a segment of the generally hollow tube is fully enclosed in the housing; the generally hollow tube having a retracted position wherein a longer segment of the tube is fully enclosed in the housing as compared to the extended position and wherein the generally hollow tube wraps around the outer surface circumference a greater number of times as compared to the extended position; wherein pulling on the proximal end and the distal end of the generally hollow tube in the retracted position is configured to cause the generally cylindrical reel to rotate relative to the housing and move the generally hollow tube to the extended position, and further wherein the proximal aperture is located in a proximal face of the housing oriented tangentially relative to the outer surface circumference, wherein the distal aperture is located in a distal face of the housing oriented tangentially relative to the outer surface circumference, the proximal and distal faces located approximately 180 degrees relative to each other and facing opposite directions.

The aforementioned embodiment may include one or more of the additional features described with the prior embodiment, including but not limited to the washer, the track including the U-shaped segment and the tabs, the spindle, the luer lock, the spike, and the feature of the housing top and bottom being removably attached to each other.

BRIEF DESCRIPTION OF THE DRAWINGS

FIG. 16 illustrates a top perspective view of a two-way retractable medical tubing reel system of another embodiment of the present invention; in FIG. 16, the top part of the housing is removed.

DETAILED DESCRIPTION

With reference to FIGS. 1-17 the present disclosure provides a two-way retractable medical tubing reel system generally designated by the numeral 10. In the drawings, not all reference numbers are included in each drawing for the sake of clarity.

Figure 5:
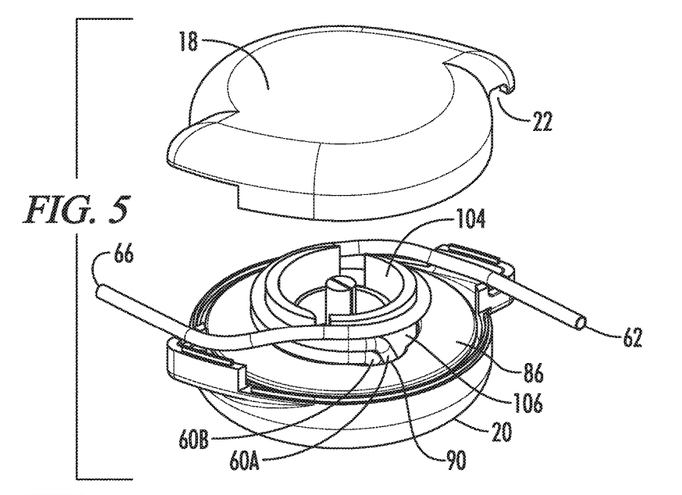
FIG. 5 illustrates a side, partially exploded perspective view of the two-way retractable medical tubing reel system of FIG. 1 without the luer lock and drip chamber.
Figure 6:
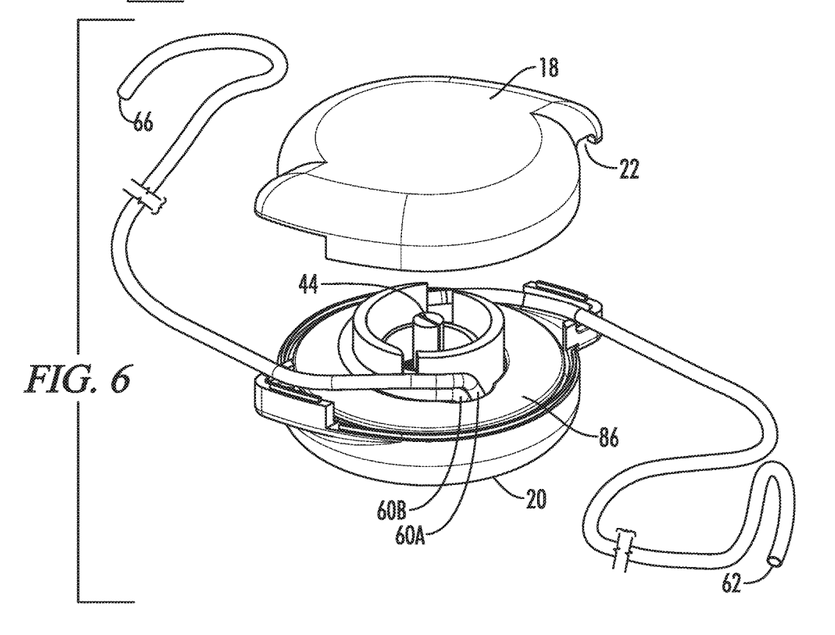
FIG. 6 illustrates a side, partially exploded perspective view of the two-way retractable medical tubing reel system of FIG. 1 without the luer lock and drip chamber; as compared to FIG. 5, in FIG. 6, the tubing is more unwound.

Referring to FIGS. 1-17, in some embodiments, the two-way retractable medical tubing reel system 10 includes a housing 12 comprising an interior 14, an exterior 16, a top 18, a bottom 20, a proximal aperture 22 and a distal aperture 24. The housing top 18 may be removable from the housing bottom 20, as seen in FIGS. 5 and 6—i.e., the housing 12 may comprise a top piece and a bottom piece that snap together.

The system 10 further includes a generally cylindrical reel/barrel 26 rotatably mounted in the housing interior 14 and having a reel wall 28 comprising an outer surface 30 having an outer surface circumference 32, an inner surface 34 having an inner surface circumference 36, a first wall aperture 38 and a second wall aperture 40, the reel wall 28 separating a reel exterior 106 from a reel interior 104—i.e., the inner surface 34 faces the reel interior 104. The first wall aperture 38 and the second wall aperture 40 may be slots in the reel wall 28.

Figure 7:
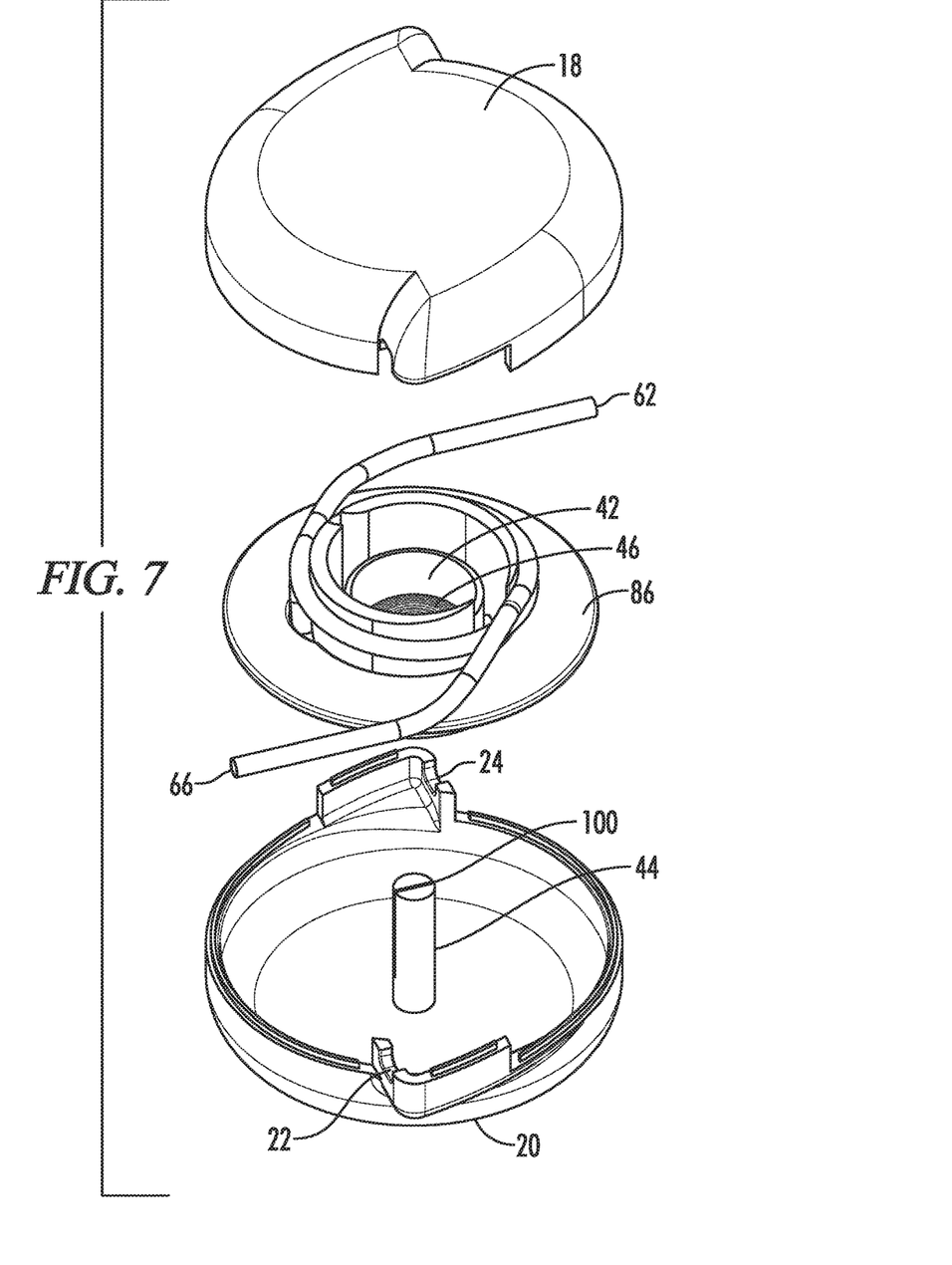
FIG. 7 illustrates a top, partially exploded perspective view of the two-way retractable medical tubing reel system of FIG. 1 without the luer lock and drip chamber.
Figure 8:
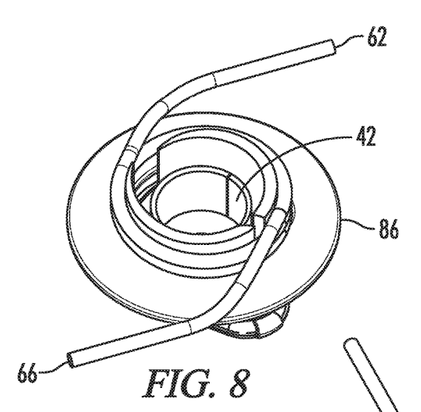
FIG. 8 illustrates a top perspective view of the two-way retractable medical tubing reel system of FIG. 1 without the housing, luer lock and drip chamber.
Figure 9:
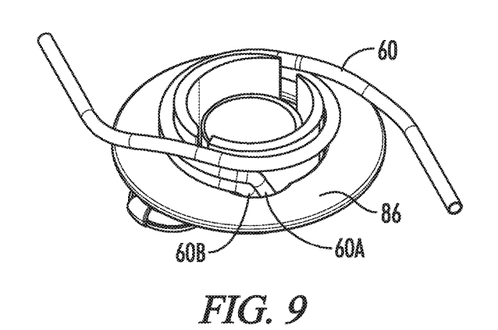
FIG. 9 illustrates another top perspective view of the two-way retractable medical tubing reel system of FIG. 1 without the housing, luer lock and drip chamber.
Figure 10:
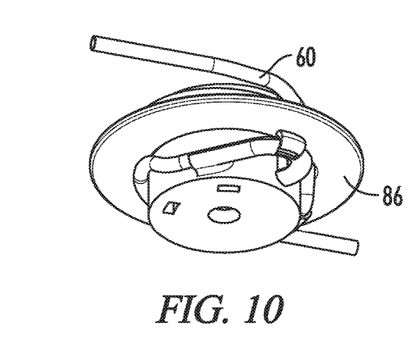
FIG. 10 illustrates a bottom perspective view of the two-way retractable medical tubing reel system of FIG. 1 without the housing, luer lock and drip chamber.
Figure 11:
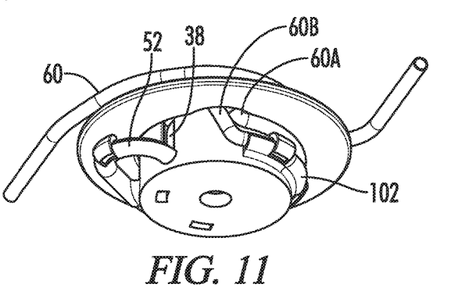
FIG. 11 illustrates another bottom perspective view of the two-way retractable medical tubing reel system of FIG. 1 without the housing, luer lock and drip chamber.
Figure 12:
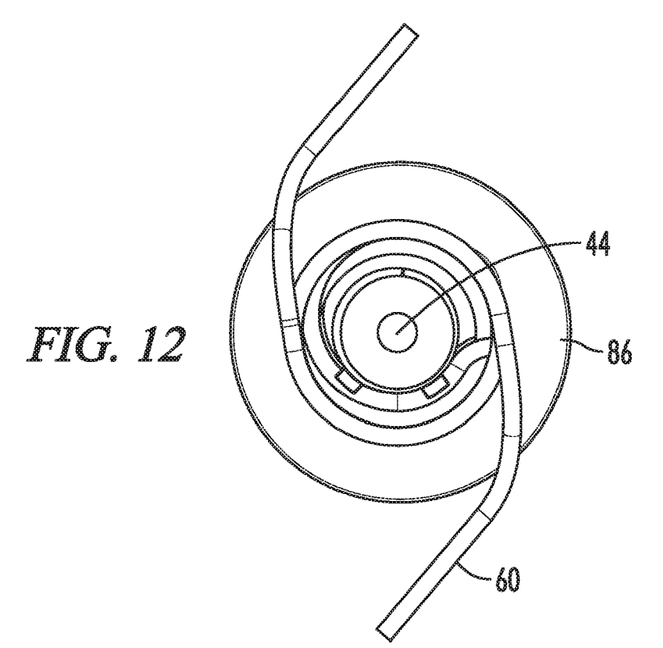
FIG. 12 illustrates a top plan view of the two-way retractable medical tubing reel system of FIG. 1 without the housing, luer lock and drip chamber.
Figures 14, 15:
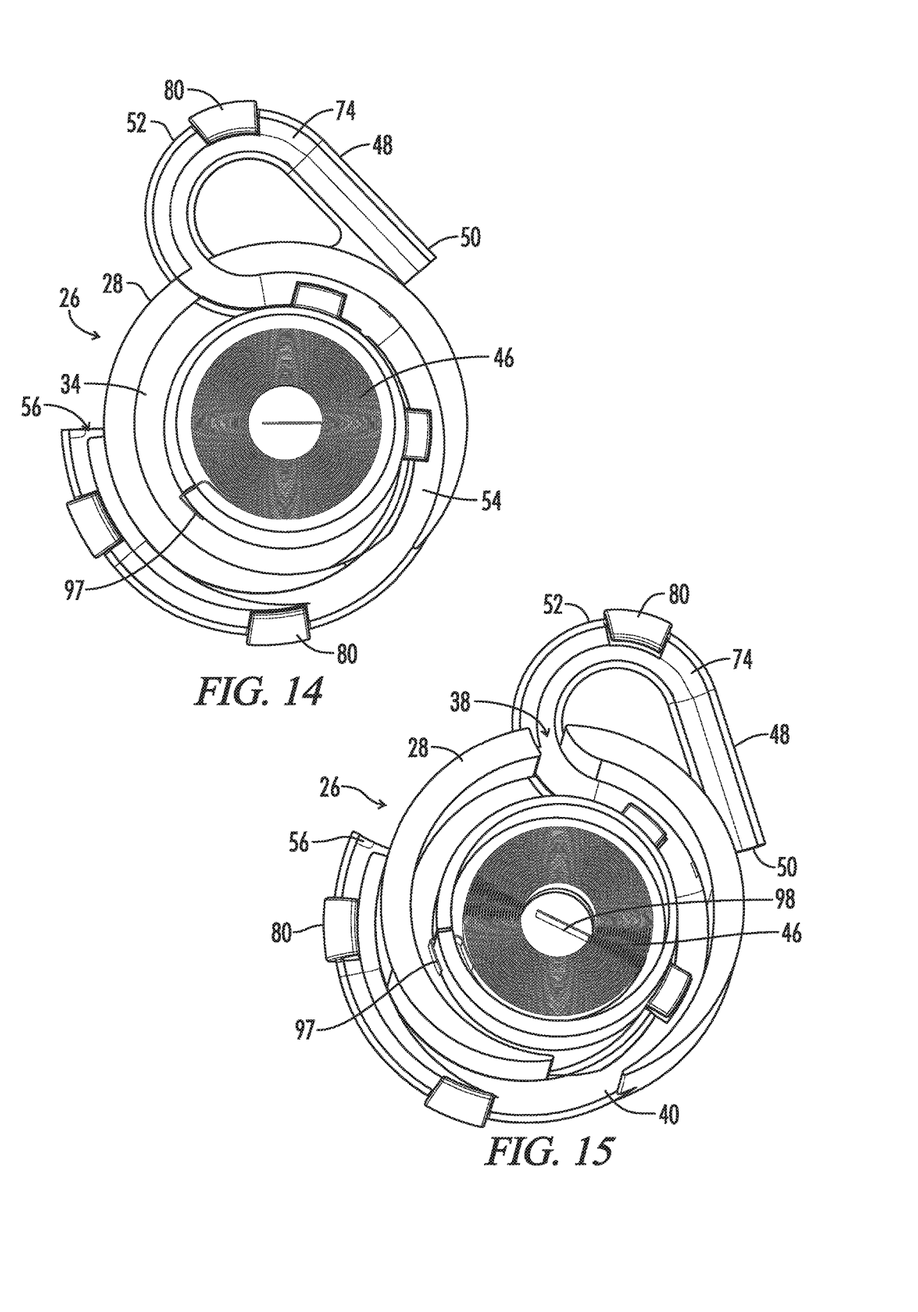
FIG. 14 illustrates a top plan view of the two-way retractable medical tubing reel system of FIG. 1 without the housing, the spindle, the washer, the generally hollow tube, the drip chamber and the luer lock.
FIG. 15 illustrates a top perspective view of the two-way retractable medical tubing reel system of FIG. 1 without the housing, the spindle, the washer, the drip chamber, the luer lock and the generally hollow tube.
Figure 16:
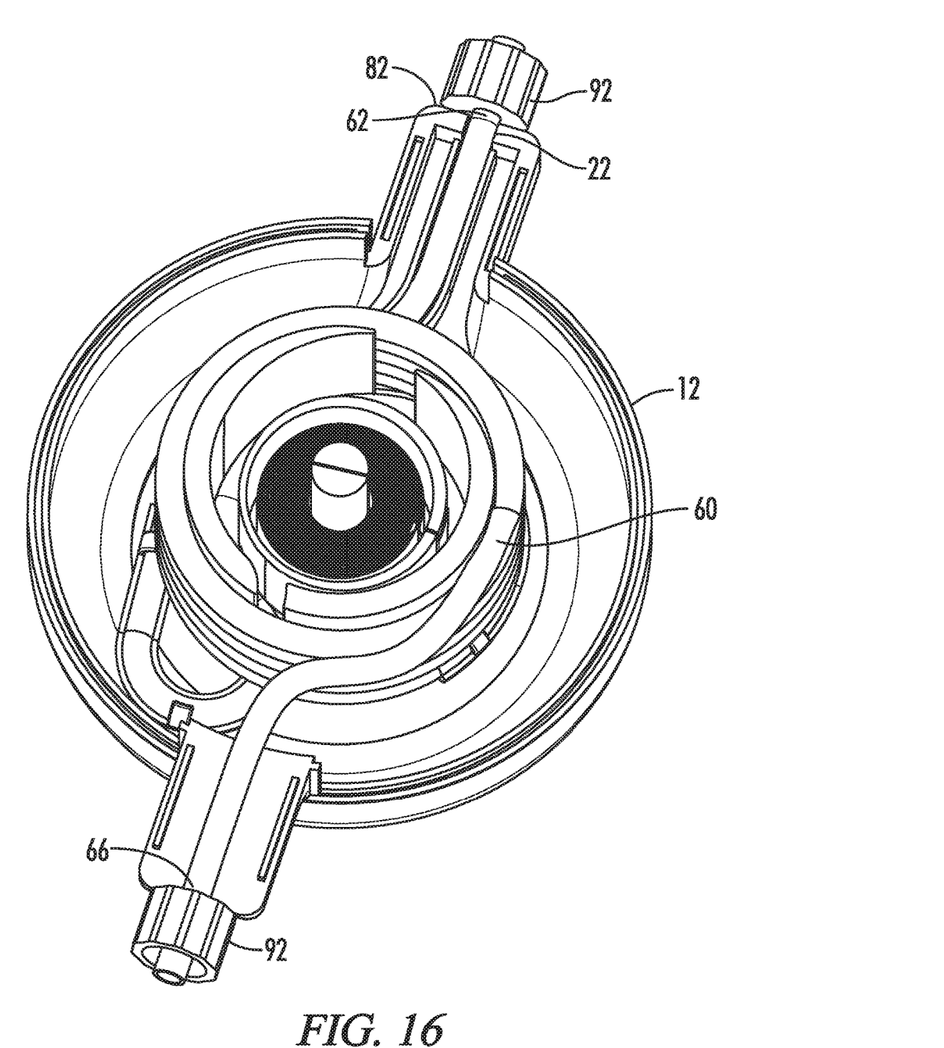
Figure 17:
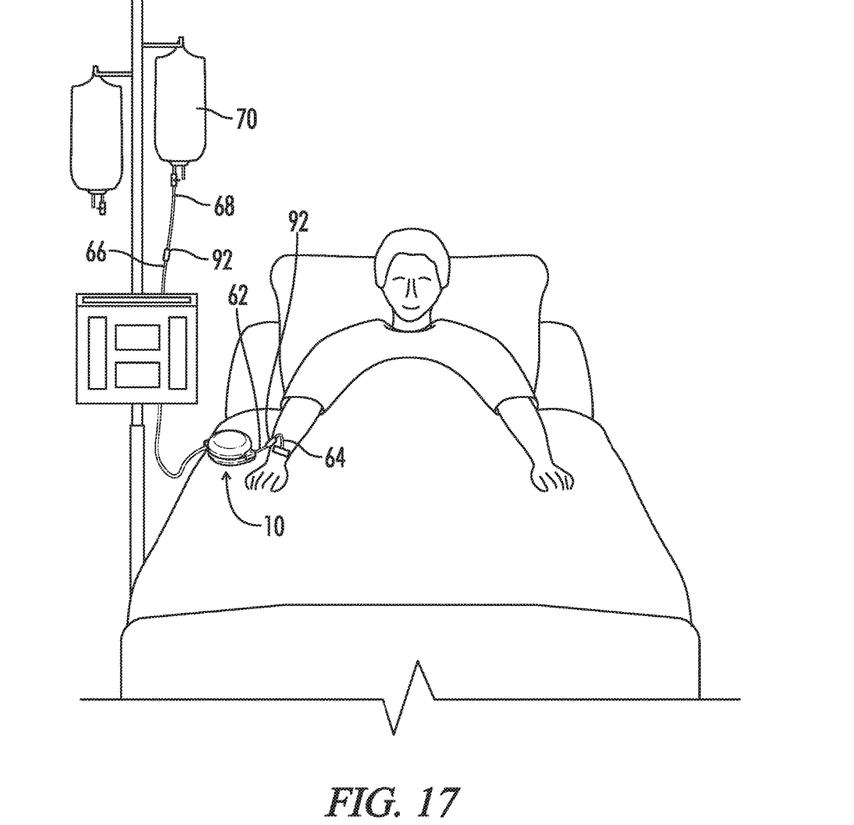
FIG. 17 illustrates a side perspective view of the two-way retractable medical tubing reel system of FIG. 1 (without the luer lock and drip chamber) connected to an IV bag and a patient.

The system 10 may further include a spindle/rod 44 that extends from the housing bottom 20 as shown in FIG. 7. When the system 10 is assembled, the spindle 44 is located (i.e., at least partially located) in the reel interior 104. The system 10 may further include a generally cylindrical spring container 42 located in the reel interior 104, the spring container 42 comprising a spring 46 attached to the spindle 44. Preferably, the spring 46 includes an inner flange 98 that attaches to a slot 100 in the spindle 44. Any suitable spring 46 may be used. In an exemplary embodiment, the spring 46 is Model No. SCP7.5D50VS sold by Vulcan Spring & Mfg. Co. (Telford, Pa.). The spring 46 may also include an outer flange 97 that attaches to the spring container 42 and causes the spring container 42 and the reel wall 28 to rotate when the tube proximal end 62 and tube distal end 66 are pulled, as best seen in FIGS. 14 and 15.

The system 10 may further include a track 48 attached to the reel wall 28 and comprising a first end 50 attached to the wall outer surface 30, a U-shaped segment 52, an internal segment 54 extending from the first wall aperture 38 to the second wall aperture 40 and located between the spring container 42 and the inner wall surface 34, a second end 56 attached to the wall outer surface 30, and a track length 58 extending from the first end 50 to the second end 56.

The system 10 may further include a generally hollow tube 60—medical tubing configured to transport medical fluids (e.g., IV fluids). The generally hollow tube 60 passes along the track length 58 and is wrapped around the outer surface circumference 32. The generally hollow tube 60 comprises a proximal end 62 configured to connect to a patient (directly or indirectly), a distal end 66 configured to connect (directly or indirectly) to an intravenous (IV) fluid bag 70, and a tube length 72 extending from the proximal end 62 to the distal end 66, the generally hollow tube 60 passing through the proximal aperture 22 and the distal aperture 24. The proximal end 62 of the generally hollow tube 60 may be attached to a drip chamber 110 and a sterile spike 112 or a fastener 92, such as a luer lock, that allows the proximal end 62 to attach to a patient tube 64 that is attached to the patient. Similarly, the distal end 66 of the generally hollow tube 60 may be attached to a drip chamber 110 and sterile spike 112 or a fastener 92, such as a luer lock, that allows the distal end 66 to attach to an IV fluid tube 68 that is attached to the IV fluid bag 70. Optionally, the proximal fastener 92 is located adjacent to the proximal aperture 22 and the distal fastener 92 is located adjacent to the distal aperture 24 when the generally hollow tube 60 is in the retracted position.

The generally hollow tube 60 is sterile so that it may be used in a hospital environment and includes a U-shaped segment 96 that is located in the U-shaped segment 52 of the track 48. The track 48 may also include a contour segment 102 located between the second end 56 and the second wall aperture 40 and the contour segment 102 may extend partially about the outer surface circumference 32, as seen in FIGS. 3, 4, 14 and 15. The track 48 and U-shaped segment 96 ensures that the generally hollow tube 60 does not kink.

Figure 1:
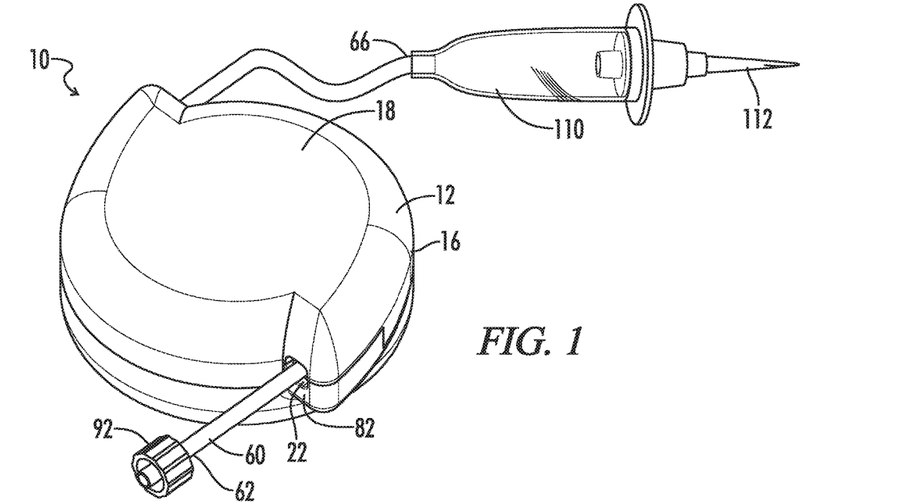
FIG. 1 illustrates a top perspective view of a two-way retractable medical tubing reel system with a luer lock attached to one end of the tube and a drip chamber attached to the other end of the tube.
Figure 2:
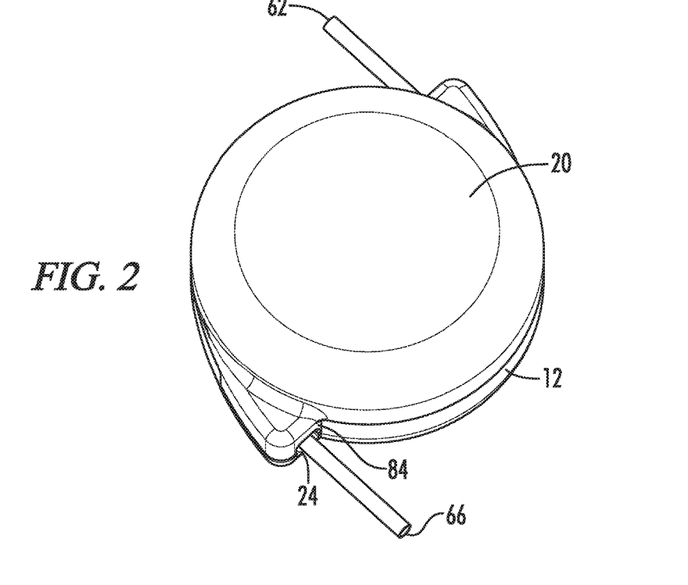
FIG. 2 illustrates a bottom perspective view of the two-way retractable medical tubing reel system of FIG. 1 without the luer lock and drip chamber.

The generally hollow tube 60 has an extended position wherein a segment of the generally hollow tube 60 is fully enclosed in the housing interior 14, as shown in FIG. 6. The generally hollow tube 60 also has a retracted position wherein a longer segment of the generally hollow tube 60 (preferably substantially all of the tube length 74) is fully enclosed in the housing interior 14, as shown in FIG. 1, FIGS. 2 and 5, as compared to the extended position and wherein the generally hollow tube 60 wraps around the outer surface circumference 32 a greater number of times as compared to the extended position. In the rested state, the generally hollow tube 60 is in the retracted position and pulling on the proximal end 62 and the distal end 66 of the generally hollow tube 60 in the retracted position is configured to cause the generally cylindrical reel 26 to rotate relative to the stationary housing 12 and move the generally hollow tube 60 to the extended position. In other words, the length of the exposed portion of the tube 60 (i.e., the length of the tube segments outside of the housing interior 14) that may be used to connect to the patient and to the IV fluid bag 70 is adjustable, providing a safer hospital environment that also provides flexibility to hospital staff in where to position the patient bed and the IV fluid bag 70.

Figure 13:
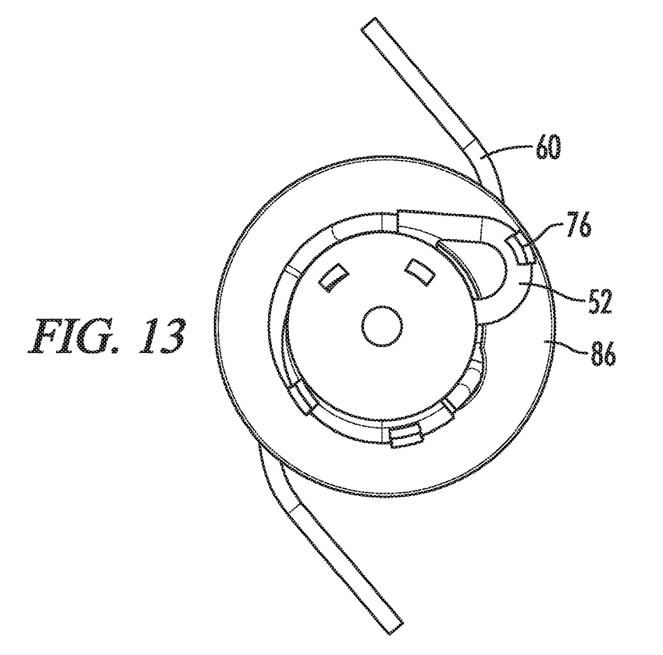
FIG. 13 illustrates a bottom plan view of the two-way retractable medical tubing reel system of FIG. 1 without the housing, luer lock, and drip chamber.

At least one of the first and second ends 50 and 56 of the track 48 (preferably, both the first and the second ends 50 and 56) are oriented tangentially relative to the reel wall 28, as best seen in FIGS. 3, 4, 11, and 14-15, and the generally hollow tube 60 wraps around the outer surface circumference 32 after exiting the at least one of the first and second ends of the track 50 and 56, as best seen in FIG. 13.

Optionally, the track 48 further comprises a floor 74 and at least one curved tab 76 having a first end 78 attached to the floor 74 and a free second end 80, the at least one curved tab 76 securing the generally hollow tube 60 to the track floor 74. In other words, the track floor 74 and the tab 76 guide the generally hollow tube 60.

Figure 3:
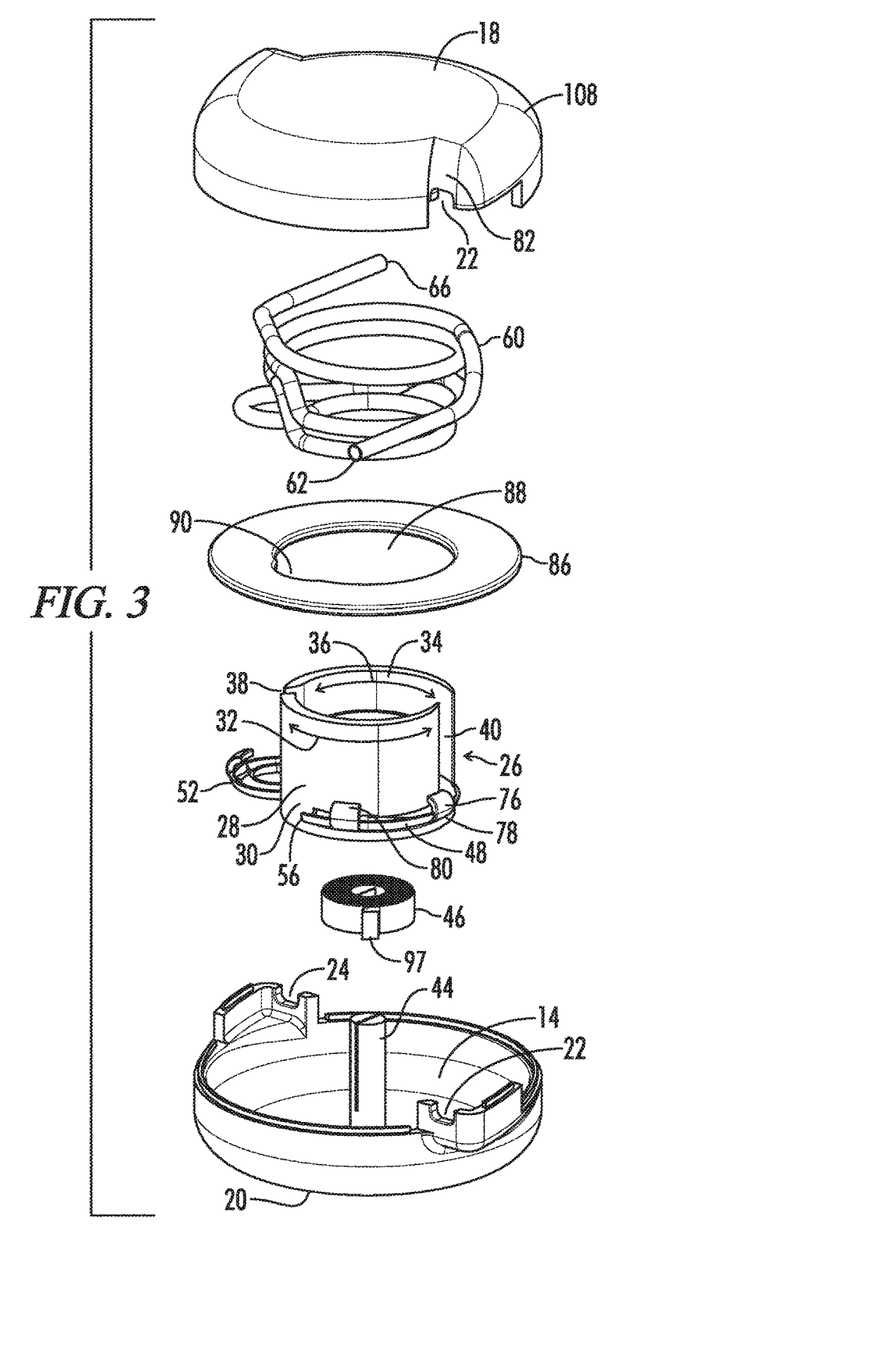
FIG. 3 illustrates a perspective, exploded perspective view of the two-way retractable medical tubing reel system of FIG. 1 without the luer lock and drip chamber.
Figure 4:
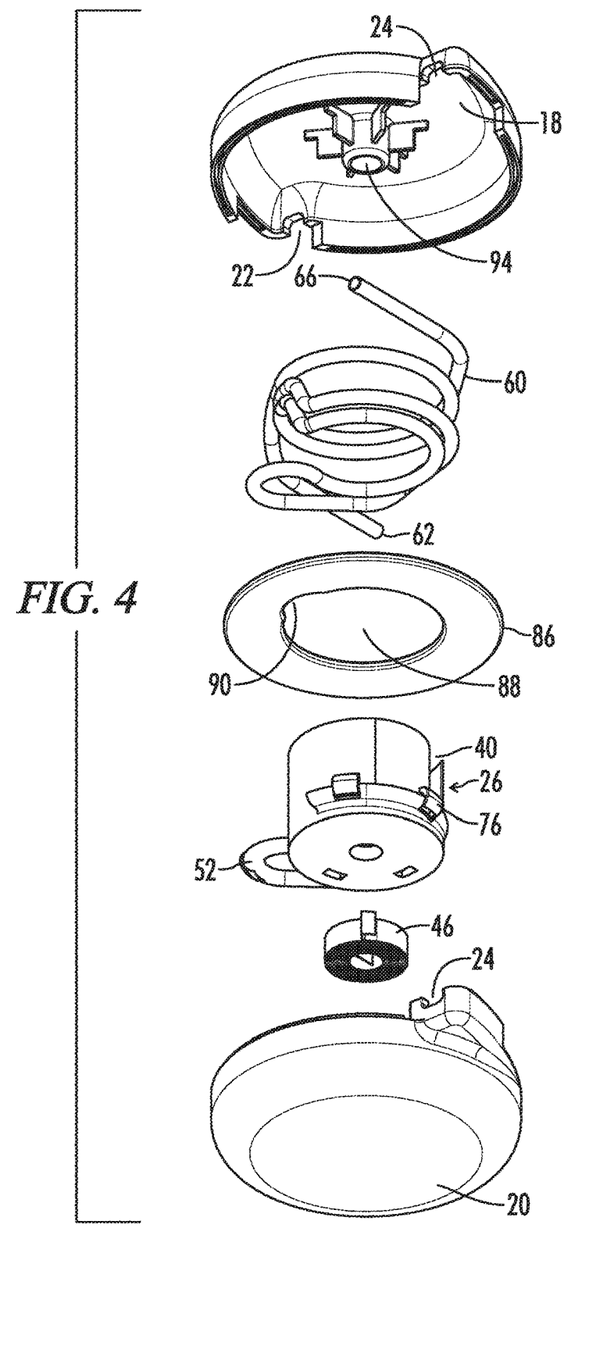
FIG. 4 illustrates a bottom, exploded perspective view of the two-way retractable medical tubing reel system of FIG. 1 without the luer lock and drip chamber.

Optionally, the proximal aperture 22 is located in a proximal face 82 of the housing 12 oriented tangentially relative to the outer surface circumference 32, as best seen in FIG. 1, the distal aperture 24 is located in a distal face 84 of the housing 12 oriented tangentially relative to the outer surface circumference 32, as best seen in FIG. 2, and the proximal and distal faces 82 and 84 are located approximately 180 degrees relative to each other and facing opposite directions, as best seen in FIGS. 3, 4, and 7. In other words, a prior design (shown in FIG. 16) had the proximal face 82 and the distal face 84 and the proximal aperture 22 and the distal aperture 24 located perpendicular to the reel outer surface 30, however, this was problematic because the generally hollow tube 60 had a tendency to kink due to the hard turn as it exited the proximal aperture 22 and the distal aperture 24. The tangential orientation of the proximal aperture 22 and the distal aperture 24 of the design shown in FIGS. 1-15 is designed to allow the generally hollow tube 60 to maintain a wrapping/circular orientation as the generally hollow tube 60 exits the proximal aperture 22 and the distal aperture 24 to avoid kinking.

Optionally, the first wall aperture 38 and the second wall aperture 40 are located approximately 180 degrees relative to each other. Optionally, the track 48 is located adjacent to the housing bottom 20. Optionally, the housing interior 14 further comprises a washer 86 located between an outer wall 108 of the housing 12 and the reel outer surface 30, the washer 86 comprising a washer aperture 88 comprising an indentation 90 located above the track second end 56 (when the housing bottom 20 is placed on a table or other surface), as seen in FIGS. 5 and 6, and further wherein two segments of the tube (labelled as 60A and 60B) are located between the indentation 90 and the reel outer surface 30, as best seen in FIGS. 5, 6, 9, and 11. The washer 86 is used to maintain the orientation of the loops (preferably the two loops) of the generally hollow tube 60 below the washer 86. The washer aperture 88 is oriented parallel to the outer surface circumference 32 and the inner surface circumference 36.

Optionally, the spindle 44 is oriented generally perpendicular to the outer surface circumference 32 and the inner surface circumference 36. In other words, the housing 12 has a height extending from the housing top 18 to the housing bottom 20 and the spindle 44 is oriented parallel to the housing height, as best seen in FIGS. 3, 6, 7. Optionally, the spindle 44 is removably received in a housing aperture 94 located in the housing top 18. The spindle 44 and the inner flange 98 do not rotate when the reel wall 28 rotates so that the spring 46 (which is attached to the spring container 42, which in turn is attached to the reel wall 28) continues to exert tension on the reel wall 28 when the generally hollow tube 60 moves to the extended position, which allows the generally hollow tube 60 to return to the retracted position when a user stops pulling on the tube proximal and distal ends 62 and 66.

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A two-way retractable medical tubing reel system comprising:
   a housing comprising an interior, an exterior, a top, a bottom, a proximal aperture and a distal aperture;
   a generally cylindrical reel rotatably mounted in the housing interior and having a reel wall comprising an outer surface having an outer surface circumference, an inner surface having an inner surface circumference, a first wall aperture and a second wall aperture, the reel wall separating a reel exterior from a reel interior;
   a spindle located in the housing interior;
   a generally cylindrical spring container located in the reel interior, the spring container comprising a spring attached to the spindle;
   a track attached to the reel wall and comprising a first end, a U-shaped segment, an internal segment, a second end, and a track length extending from the first end to the second end, wherein the internal segment extends from the first wall aperture to the second wall aperture and is located between the spring container and the inner surface of the reel wall;
   a sterile generally hollow tube located in the track and extending along the track length, the sterile generally hollow tube also wrapped around the outer surface circumference, the track comprising a proximal end configured to connect to a patient, a distal end configured to connect to an intravenous (IV) fluid bag, and a tube length extending from the proximal end to the distal end, the generally hollow tube passing through the proximal and distal apertures;
   the generally hollow tube having an extended position wherein a segment of the generally hollow tube is fully enclosed in the housing;
   the generally hollow tube having a retracted position wherein a longer segment of the tube is fully enclosed in the housing as compared to the extended position and wherein the generally hollow tube wraps around the outer surface circumference a greater number of times as compared to the extended position;
   wherein the spring is configured to bias the generally hollow tube in the retracted position;
   wherein pulling on the proximal end and the distal end of the generally hollow tube in the retracted position is configured to cause the generally cylindrical reel to rotate relative to the housing and move the generally hollow tube to the extended position.

2. The two-way retractable medical tubing reel system of claim 1 wherein at least one of the first and second ends of the track are oriented tangentially relative to the reel wall and the generally hollow tube wraps around the outer surface circumference after exiting the at least one of the first and second ends of the track.

3. The two-way retractable medical tubing reel system of claim 1 wherein the track further comprises a floor and at least one curved tab having a first end attached to the floor and a free second end, the at least one curved tab securing the generally hollow tube to the track floor.

4. The two-way retractable medical tubing reel system of claim 1, wherein the proximal aperture is located in a proximal face of the housing oriented tangentially relative to the outer surface circumference, wherein the distal aperture is located in a distal face of the housing oriented tangentially relative to the outer surface circumference, the proximal and distal faces located approximately 180 degrees relative to each other and facing opposite directions.

5. The two-way retractable medical tubing reel system of claim 1 wherein the first and second wall apertures are located approximately 180 degrees relative to each other.

6. The two-way retractable medical tubing reel system of claim 1 wherein the track is located adjacent to the housing bottom.

7. The two-way retractable medical tubing reel system of claim 1 wherein the housing interior further comprises a washer located between the housing and the reel outer surface, the washer comprising a washer aperture comprising an indentation located above the track and further wherein two segments of the tube are located between the indentation and the outer surface.

8. The two-way retractable medical tubing reel system of claim 1, wherein the proximal end of the tube comprises a proximal end tube fastener configured to removably attach the proximal end to a patient tube connected to the patient, and the distal end of the tube comprises a distal end fastener configured to removably attach the distal end to a IV tube connected to the IV bag.

9. The two-way retractable medical tubing reel system of claim 8, wherein the proximal fastener is a luer lock.

10. The two-way retractable medical tubing reel system of claim 1 wherein the generally hollow tube passes through the first wall aperture and the second wall aperture, and further wherein the generally hollow tube wraps around the outer surface of the reel wall in the same direction after passing through the first wall aperture and second wall aperture.

11. The two-way retractable medical tubing reel system of claim 1 wherein the housing top is removably attached to the housing bottom.

12. The two-way retractable medical tubing reel system of claim 1 wherein the spindle is removably received in a housing aperture located in the housing top.

13. The two-way retractable medical tubing reel system of claim 1, wherein the spindle has a spindle height generally perpendicular to the track length.

14. The two-way retractable medical tubing reel system of claim 1, wherein at least one of the proximal end and the distal end of the generally hollow tube is connected to a spike.

15. A two-way retractable medical tubing reel system comprising:
   a housing comprising an interior, an exterior, a bottom, a top, a proximal aperture and a distal aperture;
   a generally cylindrical reel rotatably mounted in the housing interior and having a reel wall comprising an outer surface having an outer surface circumference, an inner surface having an inner surface circumference, a first wall aperture and a second wall aperture, the reel wall separating a reel exterior from a reel interior;
   a spindle located in the housing interior;
   a generally cylindrical spring container located in the reel interior, the spring container comprising a spring attached to the spindle;
   a sterile generally hollow tube passing between the spring container and the inner surface, wherein the generally hollow tube passes through the first wall aperture and the second wall aperture, and further wherein the generally hollow tube wraps around the outer surface of the reel wall in the same direction after passing through the first wall aperture and second wall aperture, the generally hollow tube comprising a proximal end configured to connect to a patient, a distal end configured to connect to an intravenous (IV) fluid bag, and a tube length extending from the proximal end to the distal end, the generally hollow tube passing through the proximal and distal apertures;

the generally hollow tube having an extended position wherein a segment of the generally hollow tube is fully enclosed in the housing;

the generally hollow tube having a retracted position wherein a longer segment of the tube is fully enclosed in the housing as compared to the extended position and wherein the generally hollow tube wraps around the outer surface circumference a greater number of times as compared to the extended position;

wherein pulling on the proximal end and the distal end of the generally hollow tube in the retracted position is configured to cause the generally cylindrical reel to rotate relative to the housing and move the generally hollow tube to the extended position, and further wherein the proximal aperture is located in a proximal face of the housing oriented tangentially relative to the outer surface circumference, wherein the distal aperture is located in a distal face of the housing oriented tangentially relative to the outer surface circumference, the proximal and distal faces located approximately 180 degrees relative to each other and facing opposite directions.

16. The two-way retractable medical tubing reel system of claim 15 wherein the proximal end of the tube comprises a luer lock.

17. The two-way retractable medical tubing reel system of claim 16 wherein the distal end of the generally hollow tube is connected to a spike.

* * * * *